(12) United States Patent
Butt et al.

(10) Patent No.: US 11,524,020 B2
(45) Date of Patent: Dec. 13, 2022

(54) USE OF SOPHOROLIPIDS AS FEED ADDITIVE

(71) Applicant: DSM IP ASSETS B.V., Heerlen (NL)

(72) Inventors: Christopher Michael Butt, Kaiseraugst (CH); Pietro Celi, Kaiseraugst (CH); Norman Salem, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 346 days.

(21) Appl. No.: 16/633,390

(22) PCT Filed: Jul. 23, 2018

(86) PCT No.: PCT/EP2018/069946
§ 371 (c)(1),
(2) Date: Jan. 23, 2020

(87) PCT Pub. No.: WO2019/020578
PCT Pub. Date: Jan. 31, 2019

(65) Prior Publication Data
US 2020/0376015 A1    Dec. 3, 2020

Related U.S. Application Data

(60) Provisional application No. 62/536,821, filed on Jul. 25, 2017.

(30) Foreign Application Priority Data

Jul. 25, 2017   (EP) ..................................... 17183140

(51) Int. Cl.
| A61K 31/7028 | (2006.01) |
| A23K 20/142 | (2016.01) |
| A23K 20/158 | (2016.01) |
| A23K 20/174 | (2016.01) |
| A23K 20/189 | (2016.01) |
| A23K 20/20 | (2016.01) |
| A23K 50/75 | (2016.01) |
| A23K 10/18 | (2016.01) |
| A61P 31/00 | (2006.01) |

(52) U.S. Cl.
CPC .......... *A61K 31/7028* (2013.01); *A23K 10/18* (2016.05); *A23K 20/142* (2016.05); *A23K 20/158* (2016.05); *A23K 20/174* (2016.05); *A23K 20/189* (2016.05); *A23K 20/20* (2016.05); *A23K 50/75* (2016.05); *A61P 31/00* (2018.01)

(58) Field of Classification Search
None
See application file for complete search history.

(56) References Cited

U.S. PATENT DOCUMENTS

| 7,262,178 B2 * | 8/2007 | Gross ...................... A61P 31/04 536/4.1 |
| 2012/0142621 A1 | 6/2012 | Falus et al. |
| 2019/0037885 A1* | 2/2019 | Garnett .................. A23K 50/75 |
| 2019/0230958 A1* | 8/2019 | Michels ................. A23K 50/00 |

FOREIGN PATENT DOCUMENTS

| CN | 102696880 | 10/2012 |
| CN | 102696895 | 10/2012 |
| EP | 2 402 015 | 1/2012 |
| JP | 2010-220516 | 10/2010 |

OTHER PUBLICATIONS

Singh, S. K., Felse, A. P., Nunez, A., Foglia, T. A., & Gross, R. A. (2003). Regioselective enzyme-catalyzed synthesis of sophorolipid esters, amides, and multifunctional monomers. The Journal of Organic Chemistry, 68(14), 5466-5477. (Year: 2003).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
International Search Report for PCT/EP2018/069946, dated Oct. 17, 2018, 3 pages.
Written Opinion of the ISA for PCT/EP2018/069946, dated Oct. 17, 2018, 7 pages.

* cited by examiner

*Primary Examiner* — Dale R Miller
(74) *Attorney, Agent, or Firm* — Nixon & Vanderhye P.C.

(57) ABSTRACT

The invention relates to methods for modulation of the gut flora and/or for supporting immune system function in animals comprising administration of one or more sophorolipids to an animal in need thereof. Animal feed compositions comprising sophorolipids are also provided.

Figure 1:
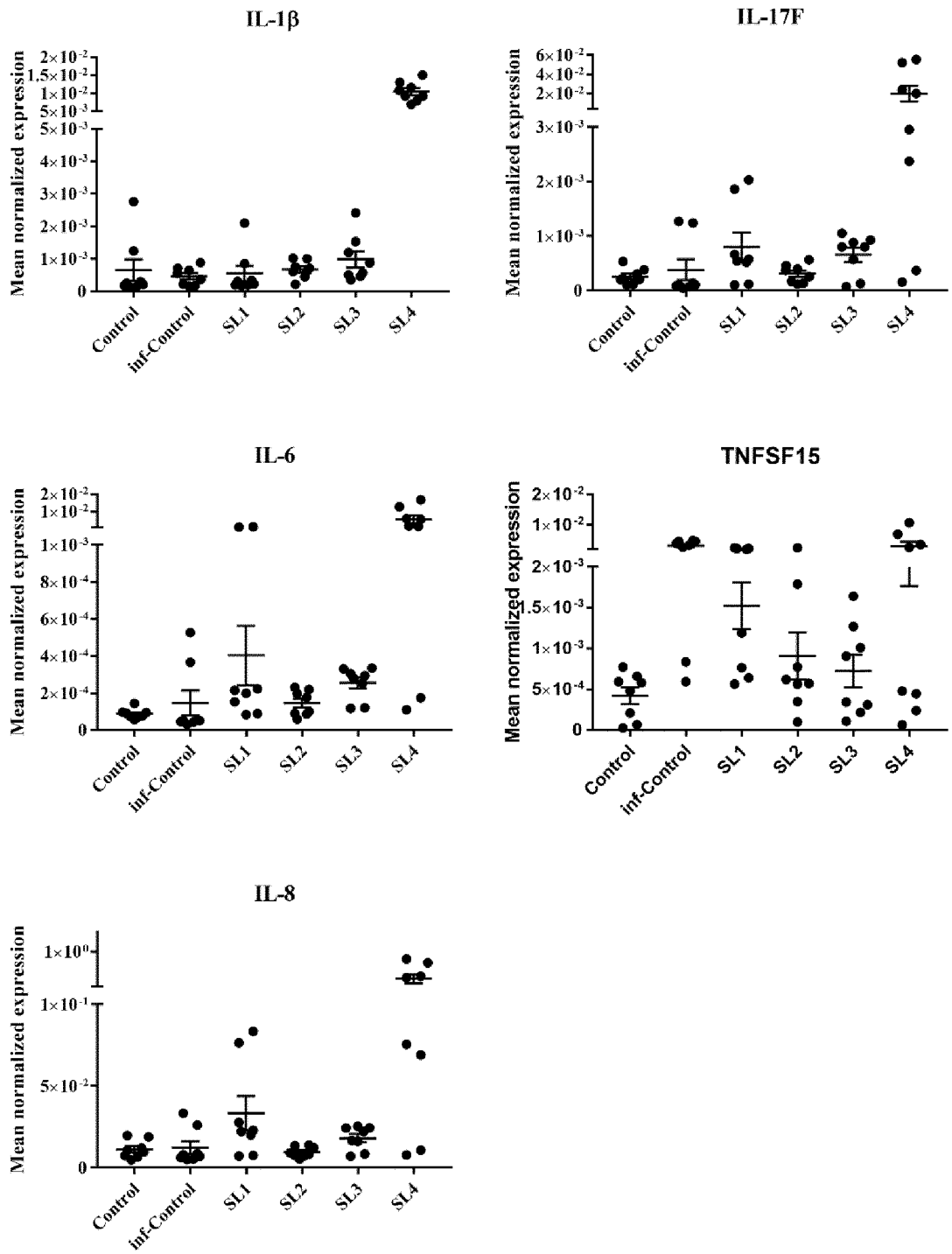

4 Claims, 8 Drawing Sheets ial phase of International
USE OF SOPHOROLIPIDS AS FEED ADDITIVE

This application is the U.S. national phase of International Application No. PCT/EP2018/069946 filed 23 Jul. 2018, which designated the U.S. and claims the benefit of U.S. Application No. 62/536,821 filed 25 Jul. 2017, and claims priority to EP Patent Application No. 17183140.7 filed 25 Jul. 2017, the entire contents of each of which are hereby incorporated by reference.

BACKGROUND

The present invention relates to feed additive compositions containing one or more sophorolipids and a method for the modulation of the gut flora and/or for supporting immune system function in animals comprising administration of one or more sophorolipids to an animal in need thereof. More particular, the present invention relates to a method for treating or preventing coccidiosis and diseases caused by *clostridium* sp. with one of more sophorolipids. The invention also relates to feed additive or feed premix compositions comprising at least one sophorolipids.

The term feed or feed composition means any compound, preparation, mixture or composition suitable for or intended for intake by an animal.

The term animal includes all animals. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include pet animals, e.g. horses, cats and dogs; mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

Sophorolipids are surface-active glycolipid compounds that can by synthesized by a select number of non-pathogenic yeast species. Sophorolipids consist of a hydrophobic fatty acid tail of 16 or 18 carbon atoms and a hydrophilic carbohydrate head, sophorose. Sophorose is a glucose disaccharide with an unusual β-1,2 bond and can by acetylated on the 6'- and/or 6"-positions. One terminal or sub-terminal hydroxylated fatty acid is β-glycosidically linked to the sophorose molecule. The carboxylic end of this fatty acid is either free (acidic or open form) or internally esterified at the 4"- or in some cases at the 6'- or 6"-position (lactonic form). The hydroxyl fatty acid itself counts in general 16 or 18 carbon atoms and can have one of more unsaturated bonds.

Due to their biodegradability and low eco-toxicity, the use of sophorolipids as bio-surfactants in industrial applications has been increasingly explored.

The present inventors now surprisingly found that sophorolipids have a great potential for use in animal feed. In particular it has been found that a composition comprising at least one sophorolipid specified hereinbelow may be used for the alleviation, cure or prevention of coccidiosis and of diseases caused by clostridium sp.

The solution to this technical problem is provided by the embodiments characterized in the claims.

BRIEF SUMMARY

The present invention relates to sophorolipids as components of animal feed or feed additives, as well as to compositions, feed additives and feed containing them. In a preferred embodiment, the one or more sophorolipids are administered orally. The one or more sophorolipids may be in the form of a feed additive composition. In another embodiment, the one or more sophorolipids are added to a feed premix product.

Therefore the present invention provides the use of said compounds as components of animal feed or feed additives.

The invention further provides the use of these compounds thereof for the preparation of compositions improving the performance of animals, especially having activity as modulators of the gastrointestinal microflora and which are applicable via animal feed.

The present invention further relates to the use of sophorolipids as hereinabove defined in the manufacture of animal feed or animal feed additive for the alleviation, cure or prevention of coccidiosis and diseases caused by *clostridium* sp—particularly *clostridium perfringens*—in animals, such as poultry.

Finally, the present invention provides animal feed additives on the basis of a sophorolipid compound according to the invention.

The term "gut" as used herein designates the gastrointestinal or digestive tract (also referred to as the alimentary canal) and it refers to the system of organs within multicellular animals which takes in food, digests it to extract energy and nutrients, and expels the remaining waste.

The term gut "microflora" as used herein refers to the natural microbial cultures residing in the gut and maintaining health by aiding in proper digestion and/or supporting immune system function.

The term "modulate" as used herein in connection with the gut microflora generally means to change, manipulate, alter, or adjust the function or status thereof in a healthy and normally functioning animal, i.e. a non-therapeutic use.

Coccidia is a generic name given to single cell protozoan organisms that are intestinal parasites that infect both vertebrates and invertebrates. The organisms cause coccidiosis, and usually settle in the small intestine, such as the colon. Infection with coccidia for farm animals can not only seriously reduce growth, but it can be life threatening. Symptoms from coccidial infection include loss of epithelial cells, the denuding of gut mucosa, and diarrhoea (often with a concomitant loss of blood). For some farm animals, such as poultry, coccidial infection can be fatal, if not seriously damaging to the animal's health.

Poultry are particularly vulnerable for coccidiosis because of several reasons: (1) The parasitic cycle of 6 to 8 days hits them at a critical stage between weeks 2 and week 4, when maximum growth is usually expressed. Since the parasites virtually destroy the whole intestinal epithelium, the absorption of nutrients is dramatically reduced, which results in marked growth depression. Until slaughter at 5 or 6 weeks, there is not enough time to recover; (2) There are 7 species of Eimeria which can infect poultry, more than in any other animal category, and at least 4 of them are regularly seen in commercial operations. Thus, when one infectious cycle is concluded already another one can be at an early stage so that coccidiosis becomes chronic; (3) In poultry the most pathogenic species (*Eimeria tenella, E. necatrix*) are observed, which induce severe hemorrhages and in certain cases can cause a mortality of up to 50%. Such an acute case of coccidiosis could easily ruin a poultry farmer; and (4) The intensive husbandry of poultry (100,000 chicks or more in one house) on deep litter facilitates access of poultry to the infectious stages of coccidia in the faeces via coprophagy and thus supports a fast spreading of the disease through a whole poultry flock. If the sanitary conditions are not rigorous, the disease will also transfer to other poultry houses on the same farm and stay on site for years.

In order to combat coccidiosis, animal feeds are often supplemented with a coccidiostat. Coccidiostats that have been approved by the EEC for use with poultry (chickens, turkeys, broilers and laying hens) include sulphonimides, amprolium, decoquinate, and ionophores. However, some of these coccidiostats are inorganic compounds that are non-natural and thus have to be made synthetically. This means that they are relatively expensive. There is therefore a need for coccidiostats that are naturally occurring.

Diseases caused by clostridium sp are common in animal stocks of poultry, pigs, rabbits and rats. There is for example, a link between the disease necrotic enteritis and the presence of clostridium perfringens. Necrotic enteritis is characterized by severe inflammation and sloughing of the intestinal tracts and often occurs together with coccidiosis.

Many articles have disclosed the amount of clostridium perfringens in the digestive tracts to have considerable impact on the health and growth rate of a broiler. Typical symptoms of infected birds are; ruffled feathers, noticeable depression, loss of appetite, loose/runny droppings or diarrhoea and a marked reluctance to move. Examples of such articles are B. S. Bains (1979) "A manual for poultry diseases" (Ed. Roche, Basel Switzerland); B Köhler, K Vogel and P Starost (1979) "Nekrotisierende und Ulzerative Enteritis bei Hühnern der Mast- und Legerichtung unter Bedingungen industriemassiger Geflügelproduktion" (Mh. Vet.-Med., 32, 704-711); B Kühler, K Vogel, W Witte and H Kühn (1983) "Vergleich der Ursachen von Hospitalismus durch *Cl. perfringens, Staphylococcus aureus* und Salmonellen unter den Bedingungen der industriemassigen Geflügelproduktion und Möglichkeiten ihrer Bekämpfung", (V. Intern. Tierhyg. Symposium, 25 und 26.05.93, Leipzig, Sammelband der Vorträge, Veterinarmedizinische Fakultät Leipzig); Th. Vissienon, U Johannsen and B Köhler (1994) "Untersuchungen zur Pathologie und Pathogenese der *Clostridium perfringens*-Typ-A-Enterotoxämie des Huhnes. 1. Versuche zur experimentellen Erzeugung der Krankheit, Versuchsansatz, klinisches Bild und Moralitätsraten", (Mh. Vet.-Med., 49, 23-28); Th. Vissienon, U Johannsen, M Solveig and B Köhler (1994) "Untersuchungen zur Pathologie und Pathogenese der *Clostridium-perfringens*-Typ-A-Enterotoxämie des Huhnes. 2. Pathomorphologische und bakteriologische Befunde nach experimenteller intraduodenaler *Cl.-perfringens*-Typ-A-Infektion" (Sporen und vegetative Keime) und Toxinapplikation (Mh. Vet.-Med., 49, 93-102).

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments and is not intended to be limiting. Instead, the scope of the present disclosure will be established by the appended claims.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

In this specification and the appended claims, the singular forms "a," "an," and "the" include plural reference unless the context clearly dictates otherwise. By way of example, "a sophorolipid" may mean one sophorolipid or more than one sophorolipid.

Unless defined otherwise, all technical and scientific terms used herein have the same meaning as commonly understood to one of ordinary skill in the art to which this disclosure belongs.

Sophorolipids contain a fatty acid tail and a carbohydrate moiety, sophorose, which is a glucose disaccharide with a 13-1,2 bond. The fatty acid tail is β-glycosidically linked to the sophorose molecule. The carboxylic end of this fatty acid may be free (the acidic or open form) or internally esterified at the 4" or at the 6' or 6"-position (the lactonic form). The fatty acid tail may have from 2 to 24 carbon atoms. Generally, the fatty acid tail has 16 or 18 carbon atoms and can have one or more unsaturated bonds. For general overviews and terminology relating to sophorolipids, see Van Bogaert et al, Appl Microbiol Biotechnol (2007) 76:23-34; Van Bogaert et al, Process Biochemistry (2011) 46:821-833; and Lang et al, Fat Sci. Technol. 1989 (91), vol. 9, 363-366. WO2004/044216 relates to the antimicrobial properties of sophorolipids and their use.

Sophorolipids can be naturally produced by certain types of yeast strains, notably *Starmerella bombicola* (also referred to as *Candida bombicola*) and *Candida apicola*. Such sophorolipids are referred to as natural sophorolipids. WO2004/044216 and WO2012/080116 describe the fermentation of natural sophorolipids in C. bombicola. WO2012/080116 also describes the isolation of sophorolipids. Such sophorolipids may be used in a method of the invention. Based on any of these publications, the skilled person understands how to produce such sophorolipids.

The term "sophorolipids" herein also encompasses modified sophorolipids. Bisht et al (J. Org. Chem. 1999, 64:780-789) describes enzyme-mediated acylation and esterification of sophorolipids. WO2004/044216 describes the chemical synthesis of several modified sophorolipids. Asmer et al (Journal of the American Oil Chemists' Society (1988), vol. 65, no. 9, 1460-1466) disclose the microbial production of sophorolipids. Sophorolipids can also be chemically modified. WO2006/069175 discloses several modified sophorolipids. The carbohydrate moiety can be alkylated, e.g. on the 6' and/or 6" positions. For example, the 6' and 6" position may be acetylated. The 6' position is identical to the 6" position except that the 6' position is closest to the fatty acid tail. Such modified sophorolipids may be used in a method of the invention. Based on any of these publications, the skilled person understands how to produce modified sophorolipids.

In some embodiments, the sophorolipid may be in the form of a free acid or ester thereof. The sophorolipid may be a sophorolipid of formula (I), wherein $R_1$ and $R_2$ are, independently, H or acetyl; $R_3$ is a $C_1$-$C_8$ alkyl group; and $R_4$ is a linear or branched, saturated or unsaturated, alkane unit comprising from 6 to 24 carbon atoms.

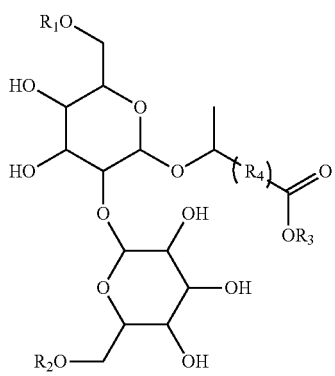

(I)

R₁ may be H or acetyl.

R₂ may be H or acetyl.

R₃ may be methyl; ethyl; propyl or isopropyl; n-butyl or isobutyl; n-pentyl, isopentyl, tert-pentyl, 2,2-dimethylpropyl; n-hexyl, 2-methylpentyl, 3-methylpentyl, 2,2 di-methylbutyl, or 2,3 di-methylbutyl; n-heptane, 2-methylhexane, 3-methylhexane, 2,2-dimethylpentane, 2,3-dimethylpentane, 2,4-dimethylpentane, 3,3-dimethylpentane, 3-ethylpentane, or 2,2,3-trimethylbutane; n-octyl, 2-methylheptane, 3-methylheptane, 4-methylheptane, 3-ethylhexane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2,2,3-trimethylpentane, 2,2,4-trimethylpentane, 2,3,3-trimethylpentane, 2,3,4-trimethylpentane, or 2,2,3,3-tetramethylbutane.

In a preferred embodiment, R₃ is an alkylester. In a preferred embodiment, the alkylester is an ethyl group or a butyl group.

R₄ may be linear or branched. R₄ may be fully saturated or may have one or more carbon-carbon double bonds. R₄ forms part of the fatty acid tail of the sophorolipid. A preferred R₄ has 15 carbon atoms. An example of a fatty acid tail having 18 carbon atoms is oleate. Eicosapentaenoic acid (EPA) is another suitable fatty acid tail. A preferred fatty acid tail is 9-octadecenoate.

In a preferred embodiment, the sophorolipid is ethyl-17-L-[(2'-0-β-D-glucopyranosyl-β-D-glucopyranosyl)-oxy]-cis-9-octadecenoate-6"-acetate, ethyl-17-L-[(2'-0-β-D-glucopyranosyl-β-D-glucopyranosyl)-oxy]-cis-9-octadecenoate-6'-acetate, ethyl-17-L-[(2'-0-β-D-glucopyranosyl-β-D-glucopyranosyl)-oxy]-cis-9-octadecenoate-6'-6"-diacetate, butyl-17-L-[(2'-0-β-D-glucopyranosyl-β-D-glucopyranosyl)-oxy]-cis-9-octadecenoate-6"-acetate, butyl-17-L-[(2'-0-β-D-glucopyranosyl-β-D-glucopyranosyly oxy]-cis-9-octadecenoate-6'-acetate, and/or butyl-17-L-[(2'-0-β-D-glucopyranosyl-β-D-glucopyranosyl)-oxy]-cis-9-octadecenoate-6'-6"-diacetate.

In some embodiments, the sophorolipid may be a 6"-mono-acetylated ethyl sophorolipid (ESL(6'OH,6"Ac) or 6B-Ac-ESL), a de-acetylated ethyl sophorolipid (ESL(6'OH,6"OH) or ESL), a di-acetylated ethyl sophorolipid (ESL(6'Ac,6"Ac) or Di-Ac-ESL), a de-acetylated butyl sophorolipid (BSL(6'OH,6"OH) or BuSL), a di-acetylated sophorolipid (LSL(6'Ac,6"Ac) or LSL), and/or a di-acetylated butyl sophorolipid (BSL(6'Ac,6"Ac) or di-acetyl BuSL).

The sophorolipids of the invention may be produced by any microorganism that naturally produces sophorolipids. Microorganisms, such as yeast, have been demonstrated to produce high levels of sophorolipids. Yeast that produce sophorolipids include, but are not limited to, *Starmerella (Candida) bombicola, Candida floricola, Candida riodocensis, Candida rugosa, Candida kuoi, Candida stellata, Candida tropicalis, Candida apicola, Torulopsis petrophilum, Rhodotorula (Candia) borgoriensis, Rhodotorula muciliginosa, Candida batistae, Torulopsis gropengiesseri, Cryptococcus* sp., *Cyberlindnera samutprakamensis, Pichia anomala, Wickerhamiella domercqiae*, and *Yarrowia lipolytica*.

Sophorolipids can be easily produced by, for example, inoculating a sophorolipid-producing yeast on a liquid medium containing carbon sources, such as vegetable oil and fat, and sugars such as glucose, and stirring the medium while aerating the medium at a mild temperature and under pressure. In a preferred embodiment, the sophorolipids are isolated and/or purified from the fermentation medium to remove fermentation by-products prior to use. Isolation and/or purification methods are known in the art. Any suitable isolation and/or purification method may be used to obtain substantially purified sophorolipids.

"Substantially free" means preferably that the corresponding impurities are present only in trace amounts, e.g. in less than 5% by weight, less than 4% by weight, less than 3% by weight, less than 2% by weight, less than 1% by weight, less than 0.5% by weight, less than 0.2% by weight, less than 0.1% by weight, less than 0.01% by weight, less than 0.001% by weight or less than 0.0001% by weight, in relation to the complete weight of the corresponding dry extract or compound of the formula I or mixture of compounds of the formula I.

In some embodiments, a microorganism that naturally produces sophorolipids may be modified to increase production of the sophorolipids of the invention.

In other embodiments, the sophorolipids of the invention may also be produced recombinantly or may be synthesized chemically.

The invention further provides a composition comprising a sophorolipid and at least one additional compound including, but not limited to, water, a solvent (such as ethanol or DMSO), an acidity regulator (such as citric acid), an anti-caking agent (such as isomalt), an antifoaming agent (such as methylethylcellulose), or mono- or di-glycerides of fatty acids), an antioxidant (such as vitamin C or sulphite), a binder (such as e.g. cyclodextrin, cross-linked sodium carboxymethyl cellulose, ethyl-, methyl-, hydroxypropyl-, hydroxypropylmethyl-, or methylethylcellulose), a bulking agent (such as cellulose, methylcellulose, or carnauba wax), a carrier (such as alginate), a colour, a surfactant, a colour retention agent, an anti-microbial (such as natamycin pediocin, nisin, levulinic acid, propionic acid, acetic acid, hops acids, and/or lauric arginate), an emulsifier (such as polyethylene glycol, triacetin, triethyl citrate, castor oil, choline salts such as choline tartrate or -lactate, xylitol, lactitol, maltitol, polydimethylsiloxane, sodium laurylsulfate, and lecithin), a preservative (such as natamycin), a dispersant (such as polyoxyethylene compounds such as polyoxyethylene sorbitan monolaurate/-monooleate/-monopalmitate/-monostearate/-tristearate, cellulose, polyvinylpyrrolidone, or propylene glycol), and a thickener (such as alginates or carrageenan).

According to the invention, the composition comprising a sophorolipid and at least one additional compound is also referred to as "the sophorolipid composition" or "feed additive composition". Examples of a sophorolipid or feed additive composition are an aqueous sophorolipid solution, an aqueous sophorolipid suspension, and an aqueous sophorolipid emulsion.

In some embodiments, the sophorolipid composition is a liquid composition. The advantage of a liquid composition is that it can be conveniently added to a feed product, particularly to a liquid feed product. The desired amount can be measured, e.g. using a measuring flask or cylinder, instead of weighed. Using a liquid sophorolipid composition allows for the sophorolipid to be dissolved more quickly or more efficiently, and to be distributed over the product more evenly. A liquid sophorolipid composition may be less prone to cake formation. A preferred liquid sophorolipid composition may comprise an emulsifier or an antifoaming agent.

Alternatively, the sophorolipid or feed additive composition is a solid composition. An advantage of a solid composition is that such composition is lighter in weight and may be more stable than a liquid composition. A solid sophorolipid composition can be dispersed in or onto a feed product. A preferred solid sophorolipid composition comprises a carrier and/or a dispersant, which components may improve the mixing properties or may facilitate dosage.

The dosages of the feed additive compositions of the present invention will be varied depending upon the requirements of the individual and will take into account factors such as animal species, age, weight, and reasons for loss of weight gain or FCR.

In practice, the feed additive composition according to the invention is added to the animal feed, either directly or as part of a blend or feed premix composition. A premix designates a preferably uniform mixture of one or more micro-ingredients with diluent and/or carrier. Premixes are used to facilitate uniform dispersion of micro-ingredients in a larger mix.

The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

In a preferred embodiment, the blend or premix composition comprises the sophorolipid or feed additive composition described above and at least one more feed ingredient.

In an embodiment, the one more feed ingredient comprises one or more enzymes, preferably as described herein below.

In an embodiment, the one more feed ingredient comprises one or more probiotics, preferably as described herein below.

In an embodiment, the one more feed ingredient comprises one or more vitamins, preferably as described herein below.

In an embodiment, the one more feed ingredient comprises one or more minerals, preferably as described herein below.

In an embodiment, the one more feed ingredient comprises one or more amino acids, preferably as described herein below.

In an embodiment, the one more feed ingredient comprises one or more prebiotics, preferably as described herein below.

In an embodiment, the one more feed ingredient comprises one or more organic acids, preferably as described herein below.

In an embodiment, the one more feed ingredient comprises one or more phytogenics, preferably as described herein below.

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, lysozyme and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the feed composition of the invention may also comprise at least one other enzyme selected from the group comprising galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any combination thereof.

In a particular embodiment, the feed composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Finase® and Quantum® Blue (AB Enzymes), OptiPhos® (Huvepharma) Phyzyme® XP (Verenium/DuPont) and Axtra® PHY (DuPont). Other preferred phytases include those described in e.g. WO 98/28408, WO 00/43503, and WO 03/066847.

In a particular embodiment, the feed composition of the invention comprises a protease (EC 3.4). Examples of commercially available proteases include Ronozyme® Pro-Act (DSM Nutritional Products).

Microbes

In an embodiment, the animal feed composition further comprises one or more additional microbes. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, *and Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, a feed premix or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, NRRL B-50136, NRRL B-50605, NRRL B-50606, NRRL B-50622 and PTA-7547.

In a more preferred embodiment, a feed premix or animal feed further comprises a bacterium from one or more of the following strains of *Bacillus pumilus*: NRRL B-50016, ATCC 700385, NRRL B-50885 or NRRL B-50886.

In a more preferred embodiment, a feed premix or animal feed further comprises a bacterium from one or more of the following strains of *Bacillus lichenformis:* NRRL B 50015, NRRL B-50621 or NRRL B-50623.

In a more preferred embodiment, a feed premix or animal feed further comprises a bacterium from one or more of the following strains of *Bacillus amyloliquefaciens*: DSM 29869, DSM 29872, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1 \times 10^{11}$ CFU/kg of dry matter. In a more preferred embodiment the bacterial count of each of the bacterial strains in the animal feed composition is between $1 \times 10^8$ and $1 \times 10^{10}$ CFU/kg of dry matter.

The bacterial count of each of the bacterial strains in the animal feed composition is between $1 \times 10^5$ and $1 \times 10^{15}$ CFU/animal/day, preferably between $1 \times 10^7$ and $1 \times 10^{13}$ CFU/animal/day, and more preferably between $1 \times 10^8$ and $1 \times 10^{12}$ CFU/animal/day. In a more preferred embodiment the bacterial count of each of the bacterial strains in the animal feed composition is between $1 \times 10^9$ and $1 \times 10^{11}$ CFU/animal/day.

In another embodiment, the one or more bacterial strains are present in the form of a stable spore.

Amino Acids

The feed composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 2001/058275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for broiler diets, respectively).

TABLE 1

| Typical vitamin recommendations | |
|---|---|
| Vitamin | Broiler diet |
| Vitamin A | 8-12,500 IU/kg feed |
| Vitamin D3 | 3000-5000 IU/kg feed |
| Vitamin E | 150-240 mg/kg feed |
| Vitamin K3 | 2-4 mg/kg feed |
| Vitamin B1 | 2-3 mg/kg feed |
| Vitamin B2 | 7-9 mg/kg feed |
| Vitamin B6 | 3-6 mg/kg feed |
| Vitamin B12 | 0.015-0.04 mg/kg feed |
| Niacin (Vitamin B3) | 50-80 mg/kg feed |
| Pantothenic acid | 10-18 mg/kg feed |
| Folic acid | 1-2 mg/kg feed |
| Biotin | 0.15-0.3 mg/kg feed |
| Choline chloride | 300-600 mg/kg feed |

Other Feed Ingredients

The feed composition of the invention may further comprise colouring agents, stabilisers, growth improving additives and aroma compounds/flavourings, polyunsaturated fatty acids (PUFAs); reactive oxygen generating species, anti-microbial peptides and anti-fungal polypeptides.

Examples of colouring agents are carotenoids such as beta-carotene, astaxanthin, and lutein.

Examples of aroma compounds/flavourings are creosol, anethol, deca-, undeca-and/or dodeca-lactones, ionones, irone, gingerol, piperidine, propylidene phatalide, butylidene phatalide, capsaicin and tannin.

Examples of stabilizing agents (e.g. acidifiers) are organic acids. Examples of these are benzoic acid (VevoVitall®, DSM Nutritional Products), formic acid, butyric acid, fumaric acid and propionic acid.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

A particular example of a blend or premix compositions of the invention comprises (a) at least one sophorolipids specified hereinabove (b) at least one fat soluble vitamin, (c) at least one water soluble vitamin, (d) at least one trace mineral, and/or (e) at least one macro mineral.

The present invention also relates to animal feed compositions comprising one or more sophorolipids of the invention. In one embodiment, the invention relates to an animal feed comprising the granule as described herein and plant based material. In one embodiment, the invention relates to an animal feed comprising the animal feed additive as described herein and plant based material.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

A preferred animal feed composition according to the invention has a crude protein content of 50-800 g/kg, and furthermore comprises at least one sophorolipids as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington DC).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal feed (or animal diets) can e.g. be manufactured as mash feed (non-pelleted) or pelleted feed. Typically, the milled feed-stuffs are mixed and sufficient amounts of essential vitamins and minerals are added according to the specifications for the species in question. Sophorolipids can be added as solid or liquid formulations. For example, for mash feed a solid or liquid sophorolipid formulation may be added before or during the ingredient mixing step. For pelleted feed the (liquid or solid), sophorolipid preparation may also be added before or during the feed ingredient step.

EXAMPLES

Sophorolipids can be analyzed by, e.g., HPLC, LC-MS or NMR spectrometry. A suitable NMR spectrometry method is as follows: approximately 5 mg of the sophorolipid and internal standard (dimethoxy benzene) can be weighed (to within 0.001 mg, with microbalance) in a 4 ml vial. The samples can be dissolved in 2 ml MeOD. 1H NMR spectra can be recorded on a 700 MHz NMR equipped with a cryo probe, measured with a probe temperature of 300K with an interpulse delay of 30 seconds and 16 scans. A suitable LC-MS methodology is as follows: Column: a reversed phase (C18) UPLC-column (1.7 μm, 100×2.1 mm (LxID) and gradient elution. The column is kept at 50° C. Gradient elution is performed by mixing 0.1% formic acid in water (A) and 0.1% formic acid in acetonitrile in the following way: 0-14 min, 40% B to 100% B; 14-17 min, 100% B; 17-17.1 min, 100% B to 40% B and 17.1-20 min, 40% B. The flowrate is 400 ul/min. Positive ion APCI mode is chosen as ionization mode for these compounds, identification is performed by high-resolution mass spectrometry. Quantification is performed by external calibration curves in combination with internal standard correction.

Example 1

Evaluation of Toxicity of Sophorolipids on Human Peripheral Blood Leukocytes (PBLs)

Cell viability was measured by Alamar Blue at various concentrations (1.25 μm, 2.5 μm, 5 μm, 10 μm, and 20 μm) of six sophorolipids: LSL(6'Ac,6"Ac); ESL(6'OH,6"Ac); ESL(6'OH,6"OH); ESL(6'Ac,6"Ac); BSL(6'0H,6"OH); and BSL(6'Ac,6"Ac).

Results: None of the sophorolipids induced toxicity at any concentration tested.

Example 2

Evaluation of Effect of Sophorolipids On Inflammatory Mediators in Human PBLs

PBLs were isolated from human blood. PBLs were treated with LPS to induce inflammatory response in the presence of different concentrations (1 μm, 5 μm, and 10 μm) of six sophorolipids: LSL(6'Ac,6"Ac); ESL(6'OH,6"Ac); ESL (6'OH,6"OH); ESL(6'Ac,6"Ac); BSL(6'0H,6"OH); and BSL (6'Ac,6"Ac).

Results: ESL(6'OH,6"OH) decreased IL-1 β secretion, IL-6 secretion, IL-8 secretion, TNF-α secretion, and MIP-1 β secretion. ESL(6'Ac,6"Ac) decreased IL-1 β secretion, IL-6 secretion, IL-8 secretion, TNF-α secretion, and MIP-1 β secretion. BSL(6'OH,6"OH) decreased IL-1 β secretion, IL-6 secretion, IL-8 secretion, TNF-α secretion, and MIP-1 β secretion. LSL(6'Ac,6"Ac) decreased IL-8 secretion, TNF-α secretion and MIP-1 β secretion. ESL(6'OH,6"Ac) decreased TNF-α secretion and MIP-1 β secretion. BSL (6'Ac,6"Ac) decreased TNF-α secretion. All six sophorolipids increased RANTES secretion.

These results demonstrate that sophorolipids have anti-inflammatory and anti-cytokine effects in PBLs.

Example 3

Evaluation of Effect of Sophorolipids on Inflammatory Mediators in Microglia

Microglial cells were obtained from primary microglial cultures from E22 rats. On day 1, microglial cells were seeded in 96-well plates and allowed to adhere for 24 hours. On day 3, the microglial cells were pre-treated with sophorolipid for 24 hours (n=11). On day 4, the microglial cells were stimulated with lipopolysaccharide (LPS). On day 5, supernatants were collected and analysed for cytokines of interest.

Sophorolipid pre-treatment was effective in reducing both PGE2 (IC50=29.8 μM) and TNF-alpha (1050=21.2 μM) secretion.

Example 4

Evaluation of Toxicity of Sophorolipids on Colon Epithelial Cells

HT-29 cells (a colon adenocarcinoma cell line) were used because these cells resemble mature intestinal cells in vitro. Cell viability was measured by Alamar Blue at various concentrations (1.25 μm, 2.5 μm, 5 μm, 10 μm, and 20 μm) of six sophorolipids : LSL(6'Ac,6"Ac); ESL(6'OH,6"Ac); ESL(6'OH,6"OH); ESL(6'Ac,6"Ac); BSL(6'OH,6"OH); and BSL(6'Ac,6"Ac).

Results: None of the sophorolipids induced toxicity at any concentration tested.

Example 5

Animal Feed Premix Composition

An animal feed premix composition is prepared by adding 20 g of at least one sophorolipids composition to the following premix (per kilo of premix):

| | |
|---|---|
| 1100000 IE | Vitamin A |
| 300000 IE | Vitamin D3 |
| 4000 IE | Vitamin E |
| 250 mg | Vitamin B1 |
| 800 mg | Vitamin B2 |
| 1200 mg | Ca-D-Panthothenate |
| 500 mg | Vitamin B6 |
| 2.5 mg | Vitamin B12 |
| 5000 mg | Niacin |
| 10000 mg | Vitamin C |
| 300 mg | Vitamin K3 |
| 15 mg | Biotin |
| 150 mg | Folic acid |
| 50004 mg | Choline chloride |
| 6000 mg | Fe |
| 3000 mg | Cu |
| 5400 mg | Zn |
| 8000 mg | Mn |
| 124 mg | I |
| 60 mg | Co |
| 29.7 mg | Se |
| 9000 mg | Lasalocid Sodium (Avatec) |
| 17.3% | Ca |
| 0.8% | Mg |
| 11.7% | Na |

Example 6

Animal Feed

A broiler grower diet having the following composition (%, w/w) is prepared by mixing the ingredients. Wheat, rye and SBM 48 are available from Moulin Moderne Hirsinque, Hirsingue, France. After mixing, the feed is pelleted at a desired temperature, e.g. about 70° C. (3×25 mm).

| | |
|---|---|
| Wheat | 46.00 |
| Rye | 15.00 |
| Soy Bean Meal (SBM 48) | 30.73 |
| Soybean oil | 4.90 |
| DL-Methionine | 0.04 |
| DCP (Di-Calcium Phosphate) | 1.65 |
| Limestone | 0.43 |
| Salt | 0.15 |
| TiO2 | 0.10 |
| Animal feed additive (above) | 1.00 |

The resulting animal feed comprises 200 mg of at least one sophorolipids composition per kg (200 ppm).

Example 7

Effect of Dietary Supplementation of Sophorolipids on Performance and Digestibility in Non-Challenged Broilers Summary: Dietary SL treatment showed a clear immunomodulatory and beneficial effects on growing commercial broiler poultry at the dose ranges we used in this trial based on various immunological analysis. SL4 clearly showed anti-parasitic effects in vivo and our preliminary in vitro data supported this conclusion. Furthermore, there was clear immunomodulatory effects of SL treatment on intestinal immune response and gut integrity.

Experimental Design

Four different Sophorolipids (SL) samples from DSM were evaluated using ARS coccidiosis and necrotic enteritis (NE) disease models using commercial broiler chickens. For each trial, negative control (uninfected and untreated) and untreated infection controls for coccidiosis and NE were included.

A total of 672 birds were used. One-day-old commercial broiler chickens were provided with ARS-formulated standard diet (Table 2) and diets supplemented with 200 ppm doses Sophorolipids as indicated in Table 1 from day 0 until the end of trial.

TABLE 1

Experimental outline-Treatment groups

| | | Challenge | Total birds | SL Inclusion level |
|---|---|---|---|---|
| Coccidiosis | Control | No | 56 | — |
| | inf-Control | Yes | 56 | — |
| | SL 1 | | 56 | 200 ppm |
| | SL 2 | | 56 | 200 ppm |
| | SL 3 | | 56 | 200 ppm |
| | SL 4 | | 56 | 200 ppm |
| Necrotic Enteritis | Control | No | 56 | — |
| | inf-Control | Yes | 56 | — |
| | SL 1 | | 56 | 200 ppm |
| | SL 2 | | 56 | 200 ppm |
| | SL 3 | | 56 | 200 ppm |
| | SL 4 | | 56 | 200 ppm |

Coccidiosis: Start with 24% CP diet

Necrotic Enteritis: Start with 18% CP diet, change to 24% after *Clostridium Perfringens* infection Materials and Methods:

Chickens:

A total 672 day-old Ross 708 male broiler chickens (newly hatched) were purchased from Longenecker's hatchery, Elizabethtown, Pa. As soon as they arrived at Beltsville ARS facility, they were divided into 12 groups in a completely randomized design and placed in the Petersime starter cages per Beltsville Animal Care guidelines, and provided with feed and water ad libitum. Birds were kept in brooder pens until 14 days of age, daily inspected for animal welfare, and were transferred to the Petersime finisher cages where they were kept until the end of the experimental period. All experimental procedures regarding transportation and infection were approved by the BARO Small Animal Care Committee.

Feed:

All chickens were provided with an antibiotic-free low protein diet (18% crude protein, dry matter basis) from day 1 to 7 and a high protein diet (24% crude protein, dry matter basis) (made at the ARS facility) from d 7 to the end of the experiment. Feed and water were given ad libitum. Feeding of supplemented treatment diet started from day 0 of age and throughout the experimental period. Feed were supplemented with antimicrobial product as shown in Table 1 according to the treatment regimen.

Method used to mix SL with standard chicken feed:

To 60 g of each sophorolipid samples which were dissolved in 100 g of Dimethyl sulfoxide, soybean oil was added to get 2000 g of total liquid volume per sample. To this, 1 g of SL was slowly added to 5 kg of feed to reach 200 ppm (0.02%) final concentration. Per weekly basis, 200 g of soybean oil was used to dissolve 6 g of SL to make 30 kg of feed mixture.

Beltsville Coccidiosis Disease Challenge Model:

At 15 days of age, birds were orally infected with $1 \times 10^4$ oocysts of *E. maxima* (Beltsville strain 41)/bird. *E. maxima* oocysts are maintained monthly by infecting 2-week-old broiler chickens orally with 10,000 sporulated *E. maxima* oocysts, and DNA tests are performed for their purity. To induce intestinal lesion and to obtain optimum oocyst shedding, we normally use 10,000 sporulated oocysts for infection and fecal oocysts shedding is examined by collecting daily oocysts from 5 dpi to 7 dpi.

Beltsville Necrotic Enteritis Disease Model:

Experimental NE model has been developed at ARS and described by Park et al., (2008). At 15 days of age, birds were orally infected with $1 \times 10^4$ oocysts of *E. maxima* (Beltsville strain 41)/bird, followed by *C. perfringens* infection ($1 \times 10^9$ CFU/bird, netB+dell strain) orally 4 days later (d 19 of age) to induce a clinical NE infection. Birds were switched to a high protein diet from d 19 of age to facilitate the development of NE.

Fecal Oocyst Collection and Counting:

Feces samples from each group were collected during 5 to 7 days post *E. maxima* infection to assess the effects of sophololipids on parasite survival. Oocyst reduction rates per each treatment group were calculated using the McMaster counting chamber.

Gut Lesion Scoring:

Coccidiosis: Lesion score was performed 5 days post *E. maxima* infection. 8 birds per group were euthanatized and approximately 20 cm jejunal intestinal segments extending 10 cm anterior and posterior to diverticulum were obtained.

Intestinal sections were scored for NE lesions on a scale of 0 (none) to 4 (high) in a blind fashioned way by six independent observers.

NE: Lesion score was performed 2 days post *C. perfringens* infection (6 days after *E. maxima* infection). 8 birds per group were euthanatized and approximately 20 cm intestinal segments extending 10 cm anterior and posterior to diverticulum were obtained. Intestinal sections were scored for NE lesions on a scale of 0 (none) to 4 (high) in a blind fashioned way by six independent observers.

Blood Samples and Chicken α-1-Acid Glycoprotein:

Blood samples were collected by cardiac puncture immediately following euthanasia on each sampling date (8 birds/trt). Serum were separated by centrifuging at 1000 rpm for 20 min at 4 C and serum fractions stored at −20 C until further use. Chicken α-1-acid glycoprotein (α-1-AGP) in serum were measured by ELISA (Life Diagnostics Inc., West Chester, Pa.) according to the manufacturer's instruction. The OD450 values were determined with an automated microplate reader (Bio-Rad, Richmond, Calif.).

Collection of Intestinal Samples:

Eight birds per treatment group were randomly selected at each sampling date and used for the collection of intestine samples (ileum) for RNA extraction to measure cytokine/chemokine and junction protein expression. Birds were euthanized by cervical dislocation and intestines were removed immediately. A small section of ileum from each bird were collected aseptically and stored in RNAlater® (Applied Biosystems, Foster City, Calif.) at −20° C. for further use.

Gene Expression Analysis by Quantitative Real-Time PCR (qRT-PCR):

The oligonucleotide primer sequences were used for qRT-PCR are shown in Table 3. The various cytokines and intestinal tight junction proteins whose differential expression were evaluated in the ileum include interleukin (IL)β, IL2, IL4, IL6, IL8, IL10, IL13, IL17F, interferon (IFN)γ, tumor necrosis factor superfamily (TNFSF)15, junctional adhesion molecule (JAM)2, occludin, zona occludens (ZO) 1, and mucin2 (MUC2). The primer sequences of TJ proteins and MUC2 were adapted from Chen et al., 2015 and shown in Table 3A. Brief description of the function of chicken cytokines/chemokines and tight junction proteins are shown in Table 3B. Glyceraldehyde-3-phosphate dehydrogenase (GAPDH) were used as the reference gene. Amplification and detection were carried out using Stratagene Mx3000P qPCR system (Agilent Technologies Inc., Santa Clara, Calif.) and RT² SYBR Green qPCR master mix (Qiagen). Each sample were analyzed in triplicates and nonspecific amplification of primers were checked by inclusion of no template controls. Standard curves were generated using $\log_{10}$ diluted RNA and the levels of individual transcripts will normalized to those of GAPDH using the Q-gene program (Muller et al., 2002).

Anticoccidial Assay:

Sporozoites of poultry *Eimeria acervulina* were freshly purified from sporulated oocysts to assess SL's cytotoxic effects on live sporozoites using the method developed in Dr. Lillehoj's laboratory. Briefly, freshly sporulated oocysts were disrupted with 0.5 mm glass beads using a Mini-bead beater (Biospec Products, USA). The released sporocysts were purified by isopycnic centrifugation in a Percoll gradient, washed in ice-cold Hank's Balanced Salt Solution (HBSS), and treated with 0.25% trypsin and 0.014 M taurocholic acid (Sigma, USA) at 41° C. to release live sporozoites. The freshly prepared sporozoites were collected by filtration, washed 3 times with HBSS at 3,000×g for 10 min at 4° C. and resuspended to $1.0 \times 10^6$/ml in HBSS. The collected sporozoites were incubated at 41° C. with various concentrations of SL samples or NK peptide as a positive control (NK lysin peptide is made in Dr. Lillehoj's laboratory and kills sporozoites) for 3 h at 41C in CO2 incubator. To access the viability of sporozoites, CyQuant direct cell proliferation assay (Thermo Fisher Scientific, USA) was carried out using live sporozoites stained with FITC and fluorescence was measured at 485/528 nm using Synergy HTX (Biotek, USA).

TABLE 2

Ingredient composition of USDA-ARS basal diet

| Ingredients (%) | Low protein | High protein |
|---|---|---|
| Corn | 69.01 | 55.78 |
| Soybean meal | 23.99 | 37.03 |
| Soybean oil | 2.75 | 2.97 |
| Dicalcium phosphate | 2.00 | 1.80 |
| Calcium carbonate | 1.40 | 1.51 |
| Salt | 0.35 | 0.38 |
| Poultry Vit Mix | 0.20 | 0.22 |
| Poultry Mineral Mix | 0.15 | 0.15 |
| DL-Methionine | 0.10 | 0.10 |
| Choline-chloride, 60% | 0.05 | 0.06 |
| Total | 100 | 100 |
| Calculated values (DM basis, %) | | |
| CP, % | 18.00 | 24.00 |
| Ca, % | 1.19 | 1.20 |
| Avail. P, % | 0.54 | 0.51 |
| Lys, % | 1.00 | 1.40 |
| Met, % | 0.42 | 0.49 |
| Cys + Met, % | 0.65 | 0.80 |
| TMEn, kcal/kg | 3585 | 3450 |

[1] Vitamin mixture provided the following nutrients per kg of diet: vitamin A, 2,000 IU; vitamin D3, 22 IU; vitamin E, 16 mg; vitamin K, 0.1 mg; vitamin B1, 3.4 mg; vitamin B2, 1.8 mg; vitamin B6, 6.4 mg; vitamin B12, 0.013 mg; biotin, 0.17 mg; pantothenic acid, 8.7 mg; folic acid, 0.8 mg; niacin, 23.8 mg.
[2] Mineral mixture provided the following nutrients per kg of diet: Fe, 400 mg; Zn, 220 mg; Mn, 180 mg; Co, 1.3 mg; Cu, 21 mg; Se, 0.2 mg.

TABLE 3

Oligonucleotide primer sequences for qRT-PCR

| Type | Target gene | Primer sequence* (5'-3') | PCR product size (Kb) |
|---|---|---|---|
| Reference | GAPDH | F-GGTGGTGCTAAGCGTGTTAT R-ACCTCTGCCATCTCTCCACA | 264 |
| Pro-inflammatory | IL1β | F-TGGGCATCAAGGGCTACA R-TCGGGTTGGTTGGTGATG | 244 |
| | IL6 | F-CAAGGTGACGGAGGAGGAC R-TGGCGAGGAGGGATTTCT | 254 |
| | IL8 | F-GGCTTGCTAGGGGAAATGA R-AGCTGACTCTGACTAGGAAACTGT | 200 |
| | IL17F | F-TGAAGACTGCCTGAACCA R-AGAGACCGATTCCTGATGT | 117 |
| | TNFSF15 | F-CCTGAGTATTCCAGCAACGCA R-ATCCACCAGCTTGATGTCACTAAC | 292 |
| Th1 | IL2 | F-TCTGGGACCACTGTATGCTCT R-ACACCAGTGGGAAACAGTATCA | 256 |
| | IFNγ | F-AGCTGACGGTGGACCTATTATT R-GGCTTTGCGCTGGATTC | 259 |

TABLE 3-continued

Oligonucleotide primer sequences for qRT-PCR

| Type | Target gene | Primer sequence* (5'-3') | PCR product size (Kb) |
|---|---|---|---|
| Th2 | IL4 | F-ACCCAGGGCATCCAGAAG R-CAGTGCCGGCAAGAAGTT | 258 |
|  | IL10 | F-CGGGAGCTGAGGGTGAA R-GTGAAGAAGCGGTGACAGC | 272 |
|  | IL13 | F-CCAGGGCATCCAGAAGC R-CAGTGCCGGCAAGAAGTT | 256 |
| TJ proteins | Occludin | F-GAGCCCAGACTACCAAAGCAA R-GCTTGATGTGGAAGAGCTTGTTG | 68 |
|  | ZO1 | F-CCGCAGTCGTTCACGATCT R-GGAGAATGTCTGGAATGGTCTGA | 63 |
|  | JAM2 | F-AGCCTCAAATGGGATTGGATT R-CATCAACTTGCATTCGCTTCA | 59 |
| Mucin | MUC2 | F-GCCTGCCCAGGAAATCAAG R-CGACAAGTTTGCTGGCACAT | 59 |

Results

1. *Eimeria maxima*-Induced Coccidiosis

TABLE 4

Lesion scores in *Eimeria maxima*-challenged group+

|  | Lesion score | |
|---|---|---|
| *Eimeria maxima* | Mean | SEM |
| Control | 0 | 0 |
| inf-Control | 1.71 | 0.34 |
| SL 1 | 1.58 | 0.24 |
| SL 2 | 1.10 | 0.09 |
| SL 3 | 1.35 | 0.21 |
| SL 4 | 1.96 | 0.24 |
| P-value |  | <0.0001 |
| inf-Control vs. SL 1 |  | >0.9999 |
| inf-Control vs. SL 2 |  | 0.5623 |
| inf-Control vs. SL 3 |  | 0.9869 |
| inf-Control vs. SL 4 |  | 0.9997 |

Summary: *E. maxima* infection-induced lesions are located in the mid-intestinal area, and these lesions show typically thicken wall with mucoid blood tinged exudates at days 5 to 6, irregular cellular debris on the outer membrane. The lesions are scored from 1 to 4 by 6 independent staff.

TABLE 5

Fecal Oocyst (*Eimeria maxima*) Production (5 to 7 dpi) in *Eimeria maxima*-challenged group

|  | Oocyst | |
|---|---|---|
| *Eimeria maxima* | Mean | SEM |
| Control | 0 | 0 |
| inf-Control | 131948 | 24088 |
| SL 1 | 104716 (↓ 21%) | 15448 |
| SL 2 | 69128 (↓ 48%) | 19394 |
| SL 3 | 70547 (↓ 47%) | 15269 |
| SL 4 | 40185 (↓ 70%) | 7489 |
| P-value |  | 0.0066 |
| inf-Control vs. SL 1 |  | 0.9578 |
| inf-Control vs. SL 2 |  | 0.1341 |

TABLE 5-continued

Fecal Oocyst (*Eimeria maxima*) Production (5 to 7 dpi) in *Eimeria maxima*-challenged group

|  | Oocyst | |
|---|---|---|
| *Eimeria maxima* | Mean | SEM |
| inf-Control vs. SL 3 |  | 0.1529 |
| inf-Control vs. SL 4 |  | 0.0061 |

*E. maxima*-infected chickens shed oocysts from days 5 into 8 days post infection with maximum. Compared to untreated infected controls, all SL-treated groups showed numerically decreased oocyst shedding (SL1-21%) reduction; SL2-48% reduction, SL3-47% reduction, SL4-70% reduction). However, only SL4 treatment showed statistically signifcant reduction in oocyst shedding. This result indicate that SL4 possesses strong anti-coccidia property.

FIG. 1 shows proinflammatory cytokine expression in ileum at 5 days post coccidiosis infection.

Following *E. maxima* infection, local cytokine response fluctuates widely. his trial was designed to look at the end point host response since all birds were sacrificed at 5 days post coccidiosis infection. At 5 days post coccidiosis infection, TNF like pro-inflammatory cytokine was increased in infected chickens. SL treatement had no effect on TNF levels. The levels of other proinflammatory cytokines such as IL-6, IL-17 and IL-8 were modulated in some SL-trated groups, especially in SL4 group strongly, and to a lesser extent, in SL2 group compared to untreated and infected group. These results suggest that SL4 and SL2 are immunomodulatory lipid.

Figure 2:
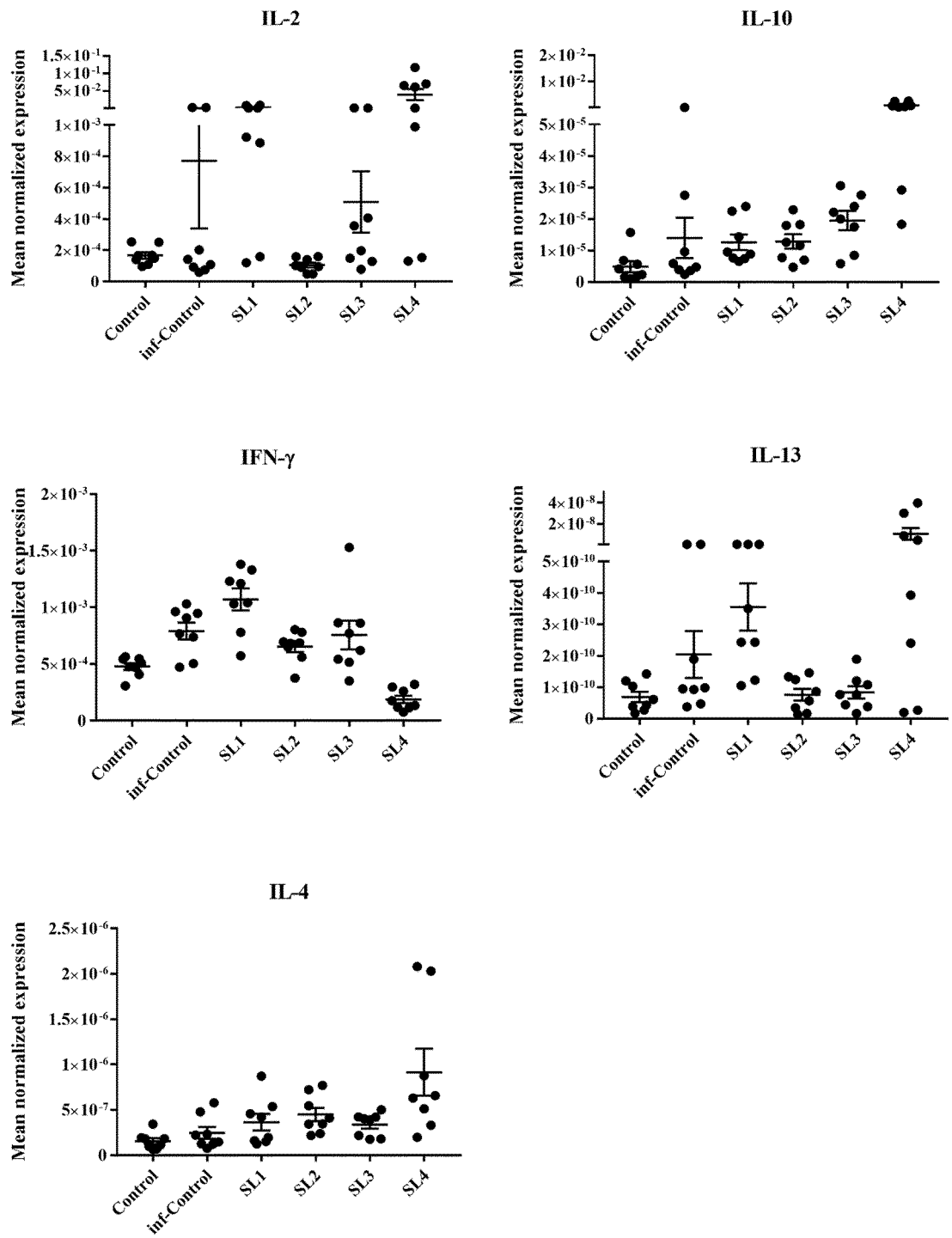

FIG. 2 shows Th1 and Th2 cytokine expressions in ileum at 5 days post coccidiosis infection Some of these SLs are immunomodulatry. SL4 stimulated IL-4, and SL2 decreased coccidis-induced IL-2, SL 2 and SL3 decreased coccidia-induced IL-13.

Figure 3:
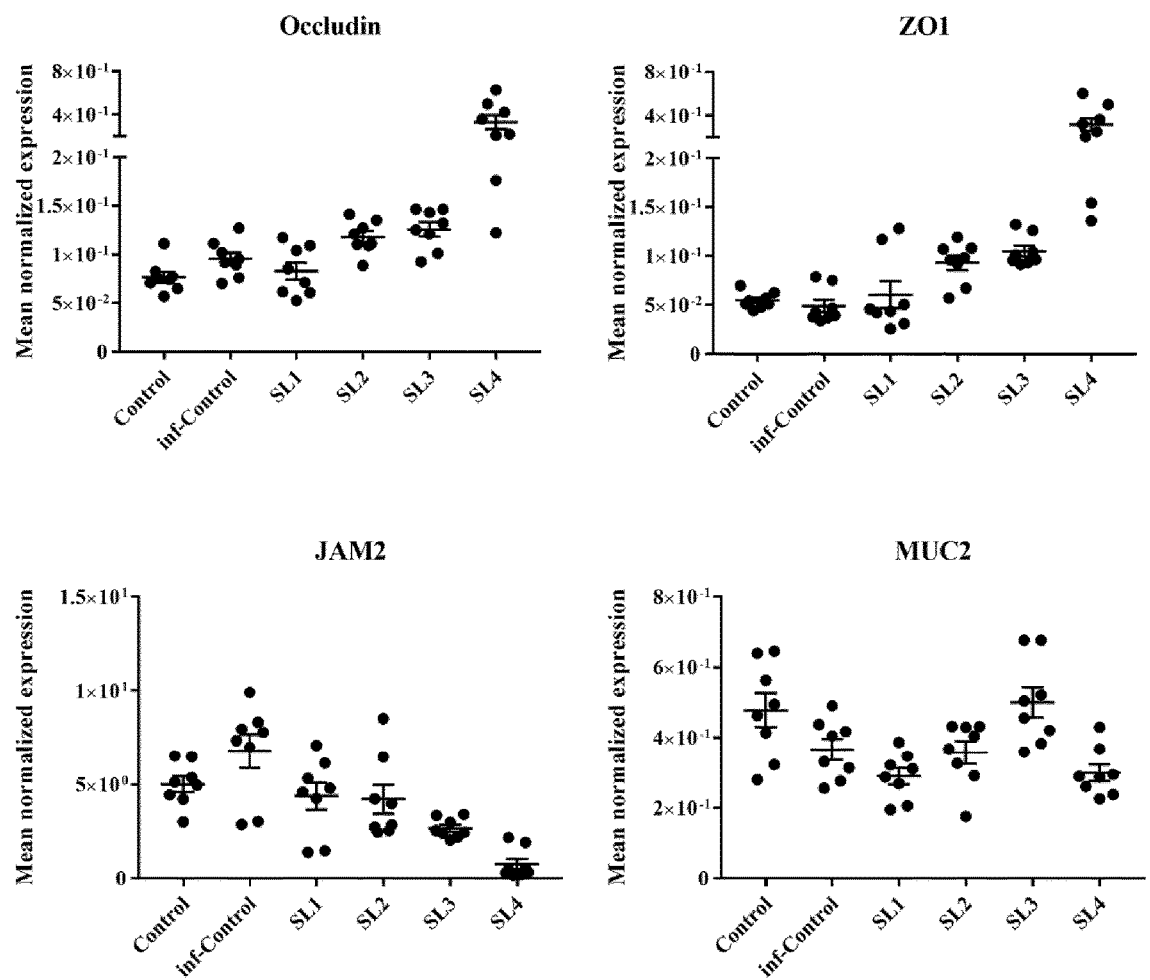

FIG. 3 shows tight junction protein expressions in ileum at 5 days post coccidiosis infection Following coccidiiosis, there is generally decreased gene expression of tight junction proteins. However, the dose of *Eimeria* we used in this study did not severely impair junction protein expression so the effects may be seen less than if severe infection was done. At 2 days post *C. perfringens* infection, SL4 enhanced two major junction protein expression, Occludin and ZO1. SL4 is clearly modulating beneficial host response by controlling expression of important protein expression following coccidiosis infection.

TABLE 6

α-1-acid glycoprotein (α-1-AGP) levels in serum at 5 days post coccidiosis infection

|  | α-1-acid glycoprotein, ng/ml | |
|---|---|---|
| *Eimeria maxima* | Mean | SEM |
| Control | 32.52 | 3.855 |
| inf-Control | 29.05 | 2.477 |
| SL 1 | 21.75 | 4.82 |
| SL 2 | 20.5 | 5.798 |
| SL 3 | 29.05 | 11.46 |
| SL 4 | 24.08 | 3.555 |
| P-value |  | P = 0.6919 |
| inf-Control vs. SL 1 |  | 0.9995 |
| inf-Control vs. SL 2 |  | 0.9973 |
| inf-Control vs. SL 3 |  | >0.9999 |
| inf-Control vs. SL 4 |  | >0.9999 |

Figure 4:
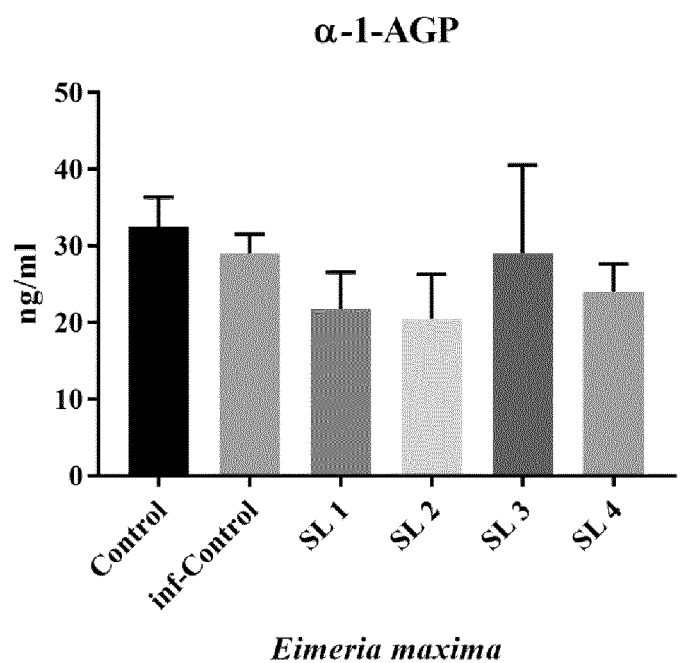

And FIG. 4 shows serum a-1-acid glycoprotein (α-1-AGP) level at 5 days post coccidiosis Summary: Commerical ELISA kit was used to measure acute phase protein levels in serum from chickens infected with *E. maxima* at 5 days post infection. The levels of this acute phase plasma alpha-globulin glycoprotein which is synthesized in the liver reflect inflammtory status post infection. Although statistically not different, birds treated with SL1 and SL2, and SL4 to a lesser extent, showed numerically reduced response.

2. Necrotic Enteritis

Figure 5:
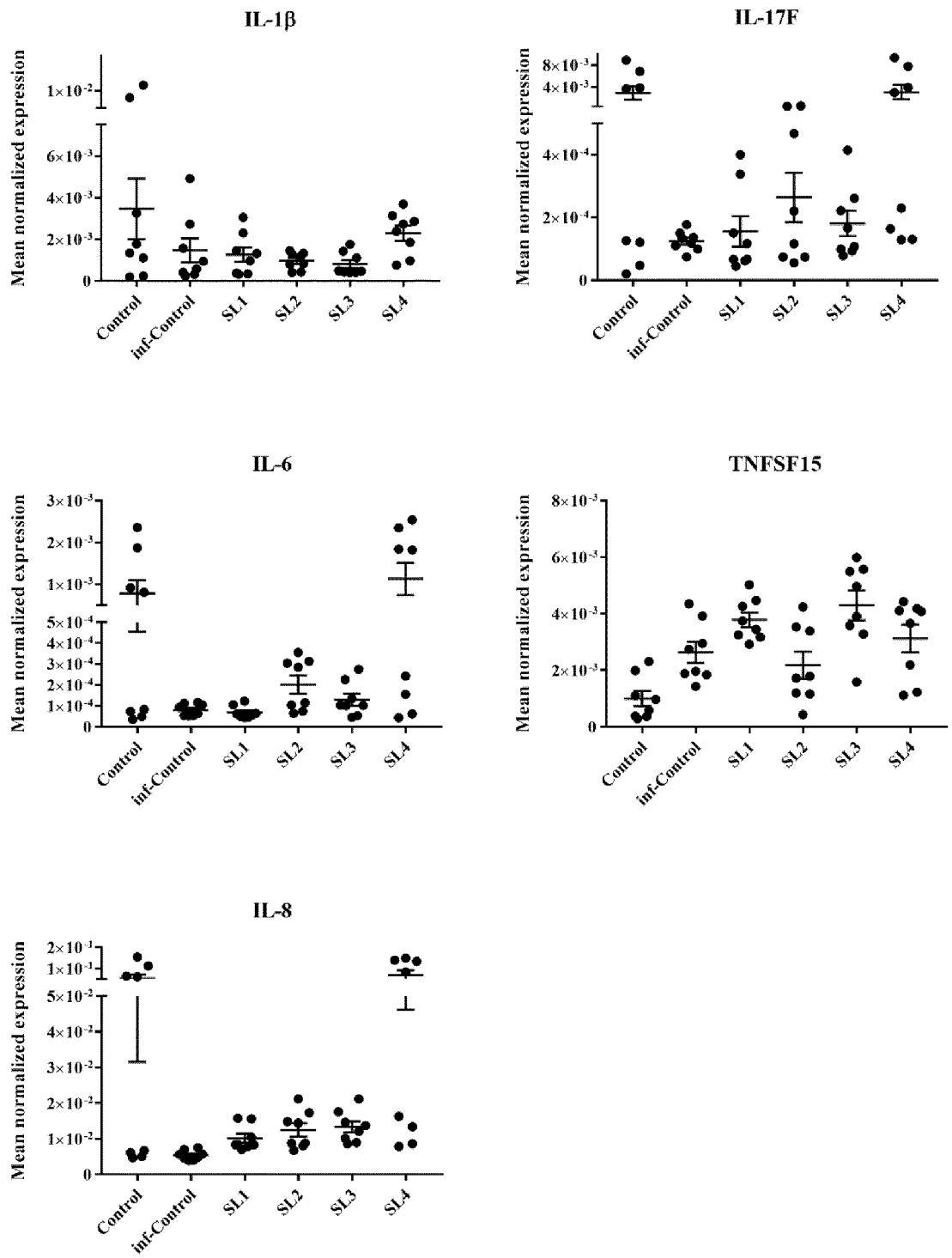

FIG. 5 shows proinflammatory cytokine expressions in ileum at 2 days post necrotic enteritis Following necrotic enteritis infection, local cytokine response fluctuates widely. Therefore, kinetic response should be examined to obtain broader view of host cytokine/chemokine response following NE infection. This trial was designed to look at the end point host response since all birds were sacrificed at 2 days post necrotic enteritis infection. At 2 days post necrotic enteritis infection, TNF like pro-inflammatory cytokine was increased in infected chickens. SL treatement had no effect on TNF levels. IL-6, IL-17 and IL-8 pro-inflammatory cytokines were decreased at 2 days post NE infection. SL modulated the levels of IL-1beta, IL-6, IL-17F, and IL-8 following NE infection with SL4 showing more stranger modulatory effects.

Figure 6:
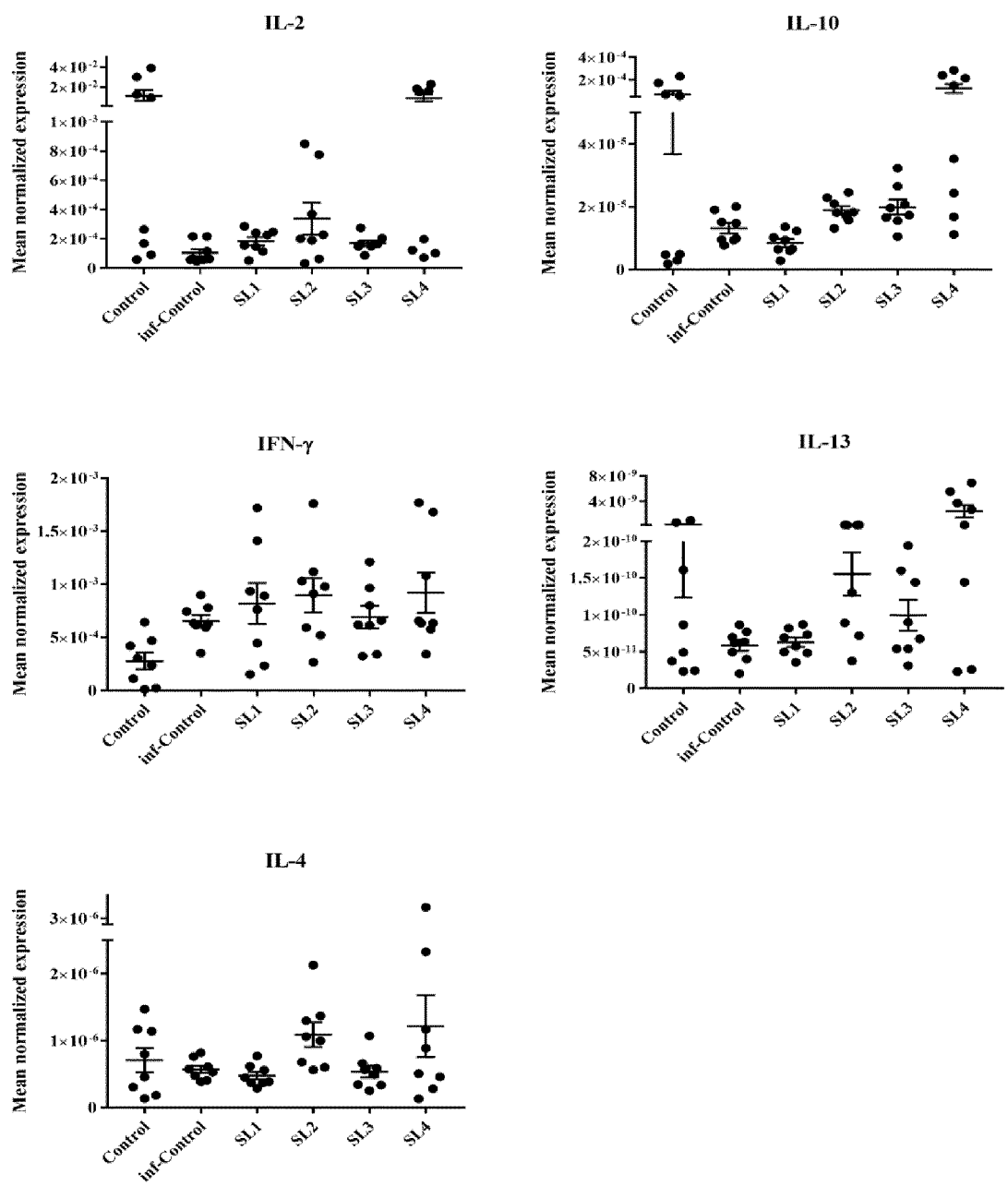

FIG. 6 shows Th1 and Th2 cytokine expressions in ileum at 2 days post *C. perfringens* infection Summary: At 2 days post necrotic enteritis infection, IL-2, IL-10, IL-13, IL-4 were modulated by SL treatement. IFN-gamma which promotes cell-mediated immunity was enahnced by SL treatement. All SL groups modulated levels of cytokine response with SL4 showing stringer effects.

Figure 7:
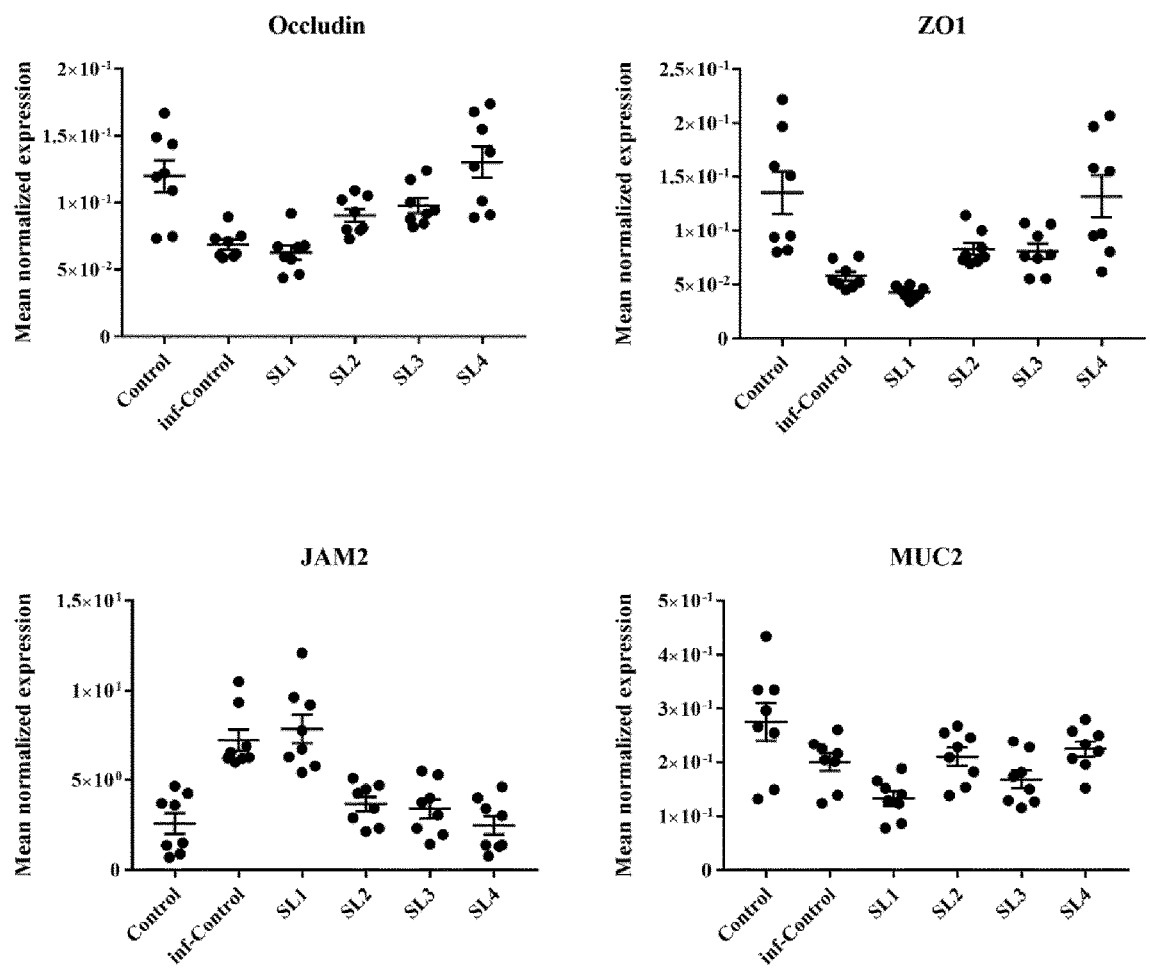

FIG. 7 shows tight junction protein expressions in ileum at 2 days post *C. perfringens* infection Summary: Following NE infection, the levels of Occuldin and ZO1 decreased in NE-infected untreated group due to gut damage. SL treatment, especially SL4 enhanced the expression of these junction proteins in the gut indicating their beneficial effect on gut integrity and gut health.

TABLE 7

α-1-acid glycoprotein (α-1-AGP) levels at 2 days post *C. perfringens* infection (necrotic enteritis) in serum

| Necrotic enteritis | α-1-acid glycoprotein, ng/ml | |
|---|---|---|
| | Mean | SEM |
| Control | 39.83 | 6.319 |
| inf-Control | 46.3 | 6.758 |
| SL 1 | 48.92 | 4.189 |
| SL 2 | 24.34 | 2.005 |
| SL 3 | 45.14 | 7.314 |
| SL 4 | 37.11 | 4.857 |
| P-value | P = 0.0391 | |
| inf-Control vs. SL 1 | >0.9999 | |
| inf-Control vs. SL 2 | 0.1089 | |
| inf-Control vs. SL 3 | >0.9999 | |
| inf-Control vs. SL 4 | 0.9861 | |

Figure 8:
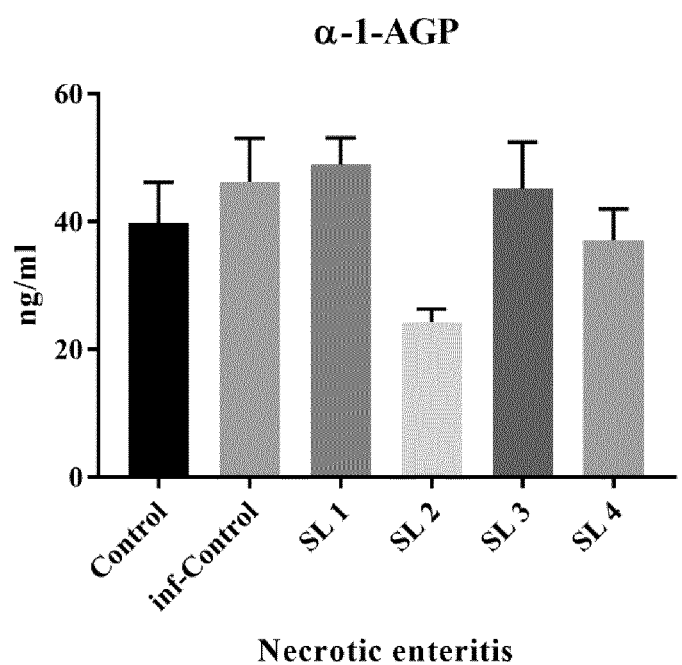

And FIG. 8 shows α-1-acid glycoprotein (α-1-AGP) in serum

Commerical ELISA kit was used to measure acute phase protein levels in serum from chickens afflicted with necrotic enteritis at 2 days post *Clostridium perfringen* s infection. The levels of this acute phase plasma alpha-globulin glycoprotein which is synthesized in the liver reflects inflammatory ststus after live infection. SL2 group showed numerically reduced response. This result indicates SL2 has ability to modulate inflammation.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method for the alleviation or treatment of coccidiosis and of diseases caused by clostridium sp. in animals, the method comprising administering one or more sophorolipids to an animal in need thereof, wherein the one or more sophorolipids is selected from the group consisting of ethyl-17-L-[2'-0-β-D-glucopyranosyl-β-D-glucopyranosyl)-oxy]-cis-9-octadecenoate-6"—acetate; ethyl-17-L-[(2'-0-β-D-glucopyranosyl-β-D-glucopyranosyl)-oxy]-cis-9-octadecenoate-6'—acetate; ethyl-17-L-[2'-0-β-D-glucopyranosyl-β-D-glucopyranosyl)-oxy]-cis-9-octadecenoate-6'-6"—diacetate;

butyl-17-L-[2'-0-β-D-glucopyranosyl-β-D-glucopyranosyl)-oxy]-cis-9-octadecenoate-6"—acetate; butyl-17-L-[2'-0-β-D-glucopyranosyl-β-D-glucopyranosyl)-oxy]-cis-9-octadecenoate-6'—acetate; and butyl-17-L-[2'-0-β-D-glucopyranosyl-β-D-glucopyranosyl)-oxy]-cis-9-octadecenoate-6'-6"—diacetate.

2. The method of claim 1, wherein the animal is a poultry animal selected from the group consisting of chicken, broiler, layer, pullet and chick.

3. The method according to claim 1, wherein the one or more sophorolipid is administered to the animal in the form of a feed additive or feed premix composition.

4. The method of claim 3, wherein the one or more sophorolipid is administered to the animal in the form of a feed premix composition which further comprises one or more components selected from the group consisting of:
a) one or more carriers;
b) one or more additional enzymes;
c) one or more microbes;
d) one or more vitamins;
e) one or more minerals;
f) one or more amino acids;
g) one of more organic acids; and
h) one or more other feed ingredients.

* * * * *